(12) United States Patent
Alkonis

(10) Patent No.: US 6,318,148 B1
(45) Date of Patent: Nov. 20, 2001

(54) TESTER FOR IMPACT PERFORMANCE

(76) Inventor: Dietrick E. Alkonis, 7351 Adam St., Paramount, CA (US) 90723

( * ) Notice: Subject to any disclaimer, the term of this patent is extended or adjusted under 35 U.S.C. 154(b) by 0 days.

(21) Appl. No.: 09/631,872

(22) Filed: Aug. 2, 2000

(51) Int. Cl.[7] .................................................. G01M 7/00
(52) U.S. Cl. ............................................................ 73/12.09
(58) Field of Search ................................. 73/12.01, 12.04, 73/12.06, 12.09; 173/90, 128

(56) References Cited

U.S. PATENT DOCUMENTS

| 4,062,411 | * | 12/1977 | Adkins et al. | 173/115 |
| 4,111,269 | * | 9/1978 | Ottestad | 173/134 |
| 6,129,300 | * | 10/2000 | Heukamp et al. | 241/191 |

* cited by examiner

*Primary Examiner*—Max Noori
(74) *Attorney, Agent, or Firm*—Donald D. Mon

(57) ABSTRACT

A tester responsive to repetitive impact blows. A brake is interposed between an impact target and a base to exert a frictional braking force on the target so the effectiveness of repetitive blows on the target can be assessed.

12 Claims, 3 Drawing Sheets

TESTER FOR IMPACT PERFORMANCE

FIELD OF THE INVENTION

A tester to test the ability of a subject to apply sufficient percussive blows to achieve a defined result within a specified time.

BACKGROUND OF THE INVENTION

In fields which require its personnel to have strength and stamina sufficient to perform certain vigorous tasks, it is not suitable to wait until the moment arrives to learn whether the person has the ability or not. Instead, tests must be devised for use during the hiring and selection process to eliminate the unqualified, as well as to be certain that the ability is retained by those who are hired.

Such tests, especially when hiring for publicly paid and competitive openings, and for retention and promotion, must be subject to standardization. This is required not only for fairness and adequacy of the test, but often by contract requirements which specify these requirements. Certainly they should be repeatable from test to test and from person to person.

An example of such a requirement is the ability of a fireman to knock a hole in a wall. The fireman must use a sledge or an axe, and in action he or she must strongly swing it with sufficient force and momentum as to break through the structure. In action, a single blow rarely accomplishes this, although it might. Instead, repeated blows are nearly always required.

Importantly, every one of the blows must be strong enough to damage the structure. Merely bouncing an axe off of a wall would be an exercise in futility. Thus, the person must have the strength to deliver sufficiently strong blows and the endurance to pound them repeatedly on the structure, each time with a damaging effect and finally with a cumulative effect. While a stronger blow is obviously better than a weaker blow, the force of each blow is not the answer. It is the accumulation of blows of damaging energy, and importantly how long it takes to get into the structure, which is in turn a function of how many blows by that person are needed. A too-long succession of lesser blows will not serve in fighting a fire. Thus, the test must measure the ability to achieve a given test result, and the time it takes to do it.

It is an object of this invention to provide a test device which can measure the person's capacity to create a given result with successive blows, and how long it takes for it.

Also, the test must be consistent from test to test and from person to person.

It is another object of this invention to provide a tester which can be calibrated before each test is started.

BRIEF DESCRIPTION OF THE INVENTION

A tester according to this invention includes a base to which a target is slidably mounted. A brake is interposed between the target and the base to resist movement of the target when it is percussively stuck. The brake is adjustable to enable its resistance to be calibrated.

A calibrator that includes a removable yoke and piston/cylinder assembly are temporarily mounted to the base so as to exert a selected static force on the target. The brake is adjusted to allow the target just to move when the calibration force is exerted, thereby to standardize the test from user to user.

The above and other features of this invention will be fully understood from the following detailed description and the accompanying drawing, in which:

DETAILED DESCRIPTION OF THE INVENTION

Figure 2:
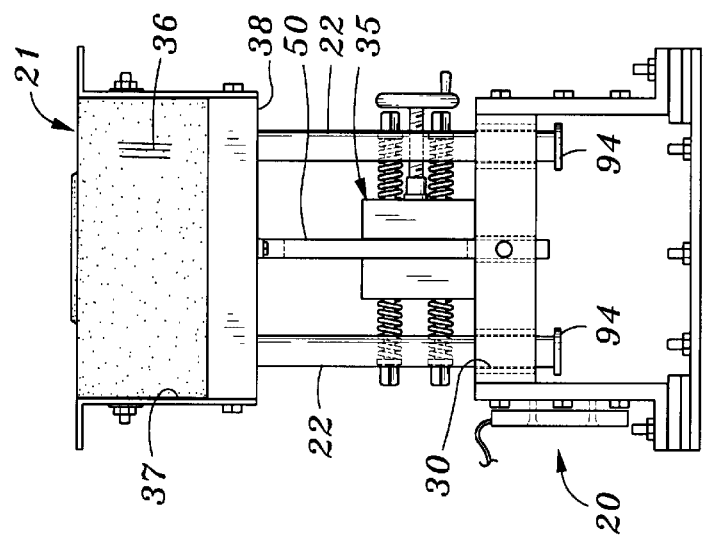
FIG. 2 is a right had side view of FIG. 1 taken at line 2—2 therein.
Figure 1:
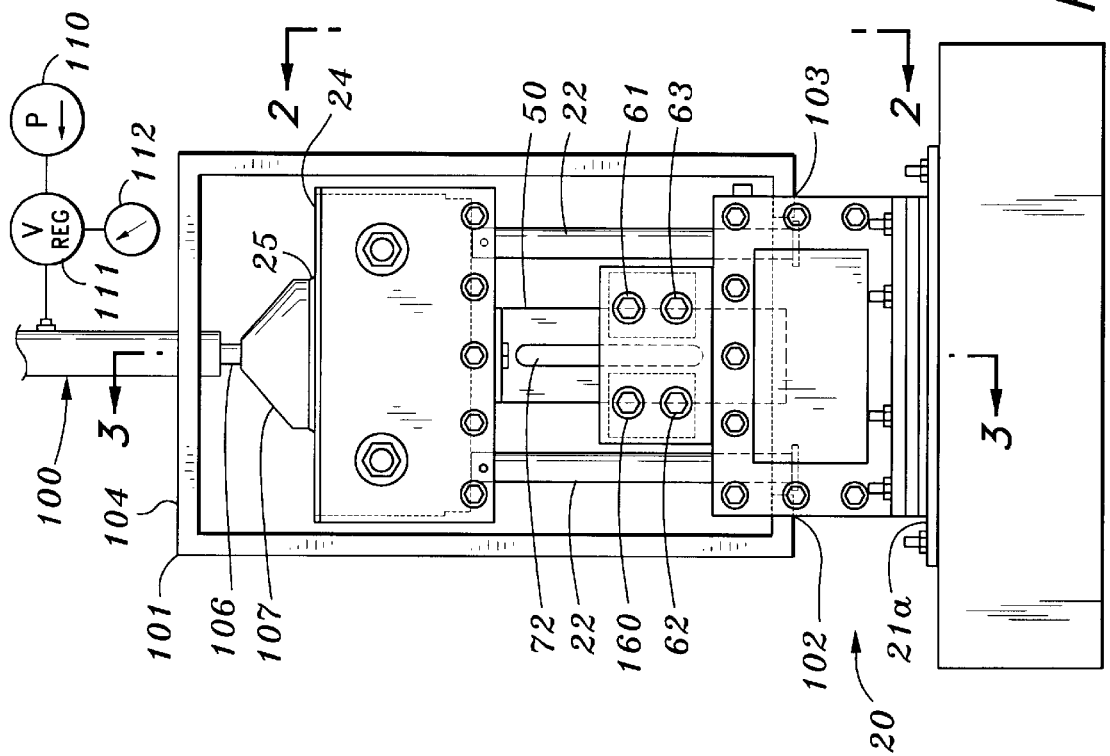
FIG. 1 is a front elevation of the preferred embodiment of the invention.
Figure 3:
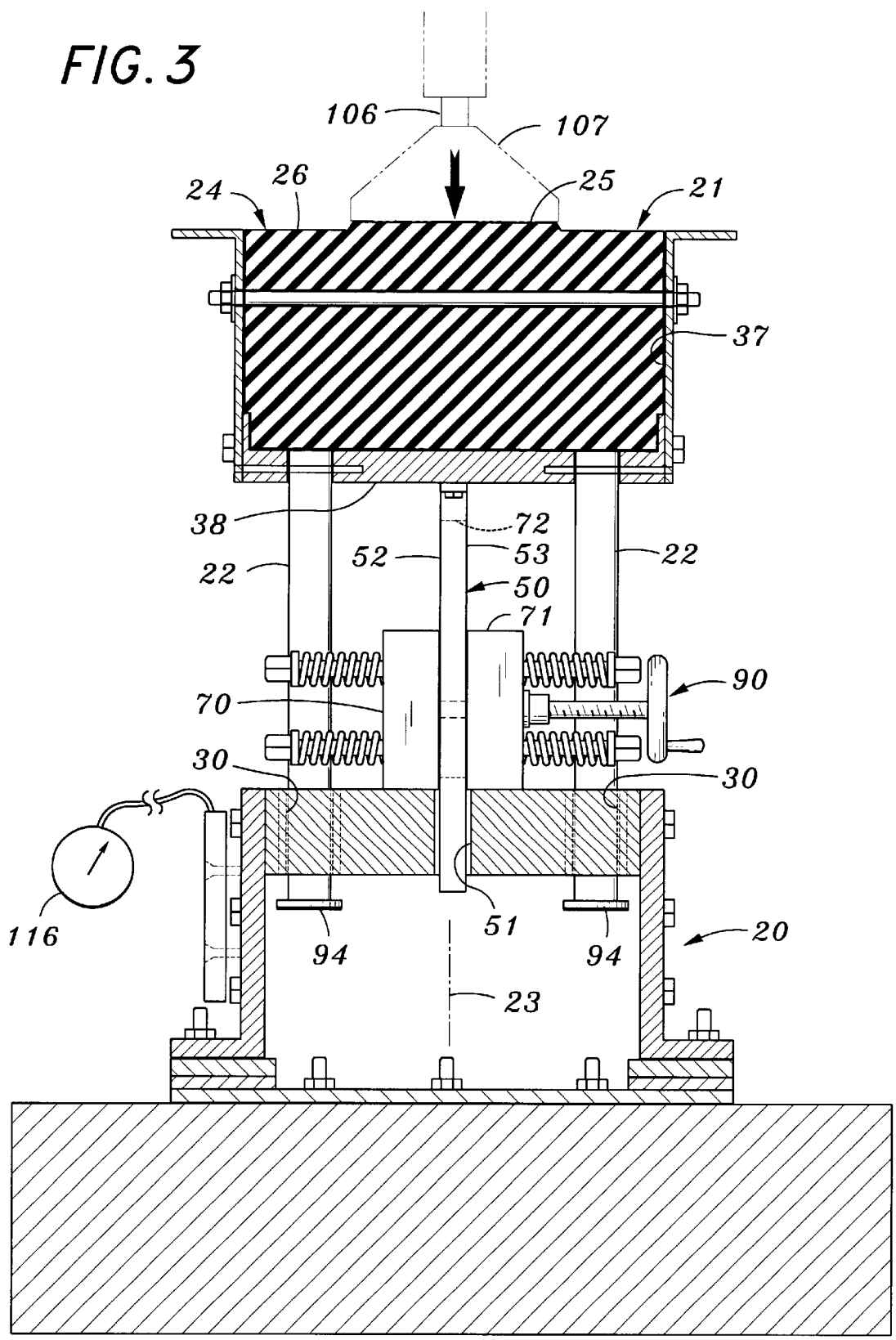
FIG. 3 is a view principally in cross-section taken at line 3—3 in FIG. 1.

The tester 20 includes a base 21a which in use will be mounted to a vertically-supporting structure (not shown) such as a wall or a very rigid and stable stand. A target 21 is mounted to four guides 22, which are aligned with a central axis 23. The target has an impact surface 24 that is normal to the axis. Circular strike pad 25 at the center of the exposed surface 26 of the target is where the tested person is expected to direct his blows.

The structure is generally rectangular. The base has four guide passages 30 that slidingly receive the guides 22. They are parallel to the axis. The objective is for the tested person to drive the target axially so the guides 22 will slide in the guide passages as the target is driven along the axis.

The axial movement of the target is resisted by a brake 35. The target itself is comprised of an impact resistant material, such as a stack of individual sheets 36 of fabric-reinforced tire material held in a tight pack by a basket-like enclosure 37. The stack is tightly compressed and is conveniently formed of layers of the material, whose upper edge is exposed to the blows. The impact surface 24 is the upper face of this stack. The bottom 38 of the basket, and the rest of the basket itself are made of strong metal so as not to be substantially deformed by the blows which are to be received.

The object of the invention is to provide means to resist the movement of the target toward the base in such a way as to reflect the capacity (ability) of the tested person to exert sufficient blows in a sufficiently limited period of time to do the work required for this movement. If he has that capacity, it will follow that he inherently has the capability to deliver blows under active conditions that would be sufficient for the purpose. In addition, as a competitive matter, the test must be consistent from person to person and to provide relative ratings.

For this purpose, a brake blade 50 is fixed, perhaps by a weldment, to the bottom of enclosure 37. It passes through a slot 51 in the base. The blade has a pair of opposite braking surfaces 52, 53. These are smooth, and are abutted by a pair of brake pads 54, 55 which bear against surfaces 52 and 53, respectively (see FIG. 4). The objective is to resist the axial movement of the target as it is driven by blows exerted on the target. This is a typical friction braking arrangement, in which the resistance is a function of applied braking pressure and the coefficient of friction.

In order to exert restraining pressure by the brake pad on the brake blades, four sets of two opposing spring bias elements 60, 61, 62, 63 are provided. These are all identical, so only element 60 and will be described in detail.

Figure 4:
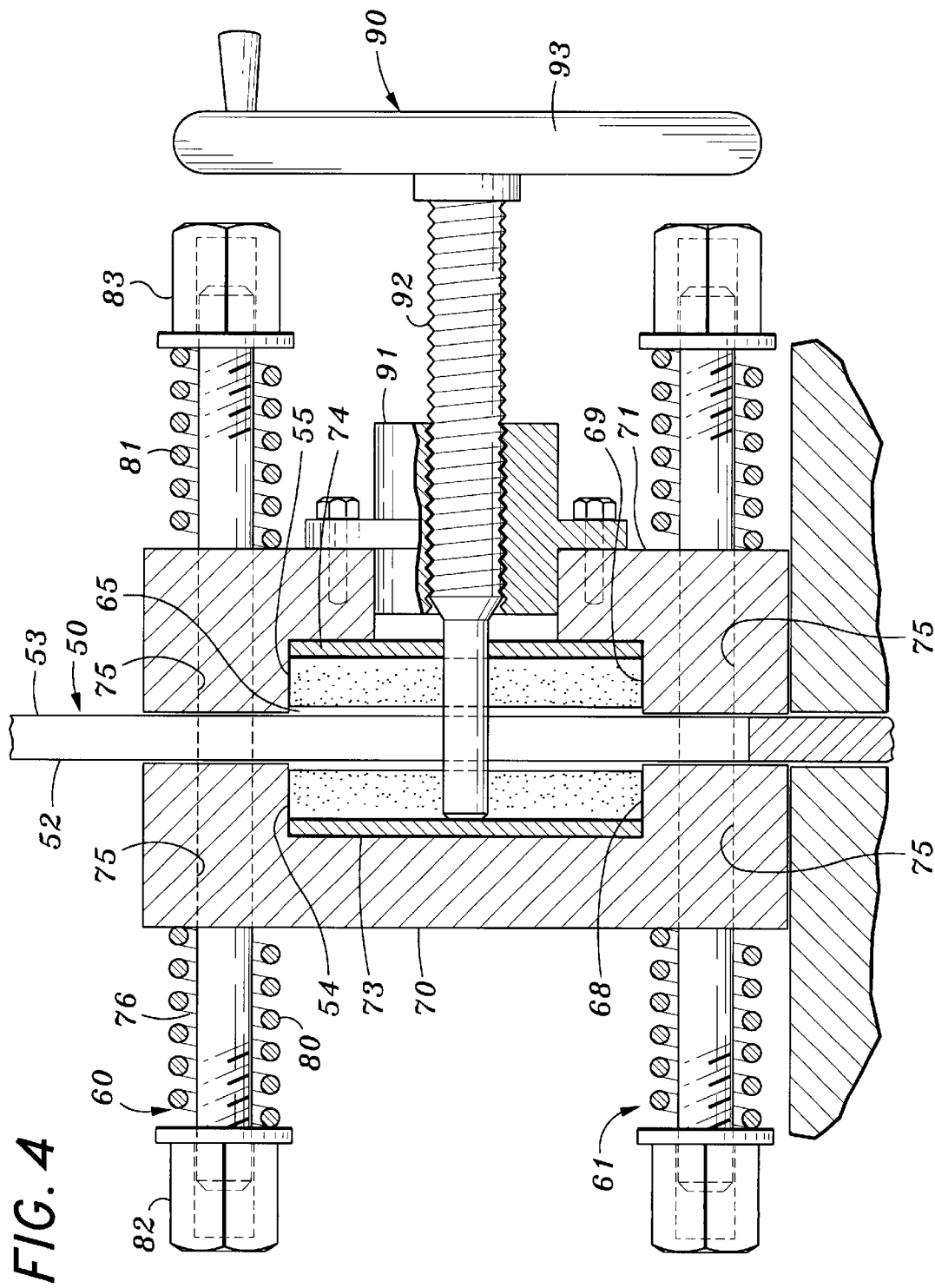
FIG. 4 is a more detailed cross-section of a portion of FIG. 3.

As best shown in FIG. 4, brake blade 50 passes through a gap 65 between brake pads 54 and 55. These pads are held in recesses 68, 69 in mounts 70, 71 respectively. The blade has an axially extending central slot 72 for a reason to be disclosed. In use, the mounts bear downwardly on the base.

The pads are backed by steel plates 73, 74. The mounts have holes 75 therethrough to pass bolts 76, these bolts being threaded on both ends. Compression springs 80, 81 surround these bolts, one on each side of the mount.

An adjustment nut 82, 83 is threaded to each end. Tightening the two nuts will compress the spring and adjustably set the pressure of the brake pads on the blade. In FIG. 4 the assembly is set in a blade-release mode, as will be seen. Thus, when the pads bear against the blade, their applied force can be adjusted by turning the nuts.

After the blade has been driven into the brake during a test, it will be tightly gripped by the brake and will be difficult to raise for the nest test. To attend to this situation, a brake release 90 is provided. A nut 91 is fixed to mount 71, and a release bolt 92 is threaded into it. It freely passes through the pads, steel plate 74, and the slot 72 in the blade, and can bear against steel plate 73. It has a suitably large hand wheel 93 to turn it. Turning the wheel will press against plate 73 and thereby push mount 70 away from mount 71 so as to release the brake. The target can then easily be raised for the next test, after which the wheel is turned the other way so as to release plate 73 from abutting contact, and the brake will then again be pressed against the blade by the springs. Stops 94 on the ends of the guides prevents the target from being lifted off the base until they are removed.

Adjusting the spring's compression will determine the braking force applied to the blade to resist axial movement of the blade and of the target.

It is desirable, but not necessary, for there to be a small angle, perhaps no more than about 5 degrees between the faces of the brake blade which preferably will be planar. This prevents a too-free passage of the blade along the brake pads. As a consequence, the driving force needed may be somewhat greater as the target is driven further.

It will be appreciated that unless there is a sufficient braking force, the target would supply slip downwardly and nothing could be learned. The object is to set the braking force at such a level that a suitable test subject would be able to drive the target to its destination in a given time.

There is no definitive way to adjust this device. Instead it must be calibrated to reflect the needs felt by senior and experienced men, such as fire captains who have had years of experience and know "in their bones" what it takes. This device can be set (calibrated) to recognize their opinion as to sufficiency. Then all similar devices can be set the same.

For this purpose, a calibrator 100 with removable yoke 101 can be hooked to attachments 102, 103 on the base, with a bight 104 that overhangs the target when in place. A hydraulic (or pneumatic) cylinder 105 is fixed to the bight. A piston rod 106 attached to a piston (not shown) extends from the cylinder and bears against a foot 107 which in turns bears against the target.

A source 110 of fluid pressure such as a gas bottle or a pump provides fluid through a pressure regulator 111 and gauge 112 to the cylinder. Next the brake is tightened with the target raised. A selected pressure is applied, leading to an applied force on the target from the foot. At some pressure and setting of the brake, the target will begin slowly to move. The calibration will, of course, be removed when the target is to be struck.

Now the person calibrating the device has a place to start. With the brake setting and the known pressure, he removes the yoke and beats on the target with a selected implement. If it is too easy, he will know. Also he will know if it is too difficult. There will follow a few more adjustments of tightening or loosening the bias and of changing the pressure. Best procedure will be to select some fluid pressure, perhaps 700 psi, and adjust the brake pad bias.

Soon the device will feel right to an experienced man who is pounding on the target. The fluid pressure setting can be agreed on. Then from device to device, and from test to test, the brake bias will be set so as just to start moving at that pressure when the foot is in place. Now there exists a readily repeatable and reliable tester that reflects the needs of a suitable person such as a fire fighter. Notice that with an agreed pressure, there is only the need to adjust the spring forces on the brake.

Because completion of the test involves applying sufficient blows of sufficient strength within a specified time period, a limit switch 115 or other type of sensor is mounted where it will be contacted by a target driven through a sufficient distance. A timer 116 can be coupled to the limit switch to indicate how long it took for the switch to be closed. There results a tester useful to determine whether a person can, within a stated time, achiever a desired result with repeated precussive blows.

While measuring the ability to knock a hole in a wall is the presently-known best use for this device, it is also useful for testing the capacity to perform other functions which include percussive blows.

This invention is not to be limited by the embodiment shown in the drawings and described in the description, which is given by way of example and not of limitation, but only in accordance with the scope of the appended claims.

I claim:

1. A tester responsive to repetitive impact blows, comprising:
    a base establishing an impact axis;
    an impact target mounted to said base for axial movement toward said base, said target having a surface intended to receive impact blows;
    a brake comprising a blade mounted to said target, and a brake pad mounted to said base, said brake pad being resiliently mounted to exert a frictional braking force on said target, the braking force of said brake being adjustable.

2. A tester according to claim 1 in which springs are so disposed and arranged as adjustably to bias the brake pads against the blade, whereby to adjust said braking force.

3. A tester according to claim 2 in which a sensor is fixed to the base, so disposed and arranged as to signal the arrival of the holder at a desired limit.

4. A tester according to claim 2 in which a brake release is mounted to said base to release the brake pads from the blade to enable the target to be moved to a start position.

5. A tester according to claim 4 in which said blade includes an axial slot through which the brake release passes.

6. A tester according to claim 2 in which said brake pads are held in respective mounts one on each side of said blade, and in which a bolt passes through both of said mounts with a nut threaded to both ends and a spring between each nut and the respective mount, whereby when the nuts are tightened, the compressive force on the brake pads is adjustably increased.

7. In combination:
    a tester according to claim 1; and
    a calibration device comprising a detachable yoke attachable to said base, said yoke having a central bight, a cylinder fixed to said bight, a piston in said cylinder, a piston rod mounted to said piston and extending beyond said cylinder, a foot on said rod adapted to bear against said target to exert an axial force on the target, a source of fluid under pressure connected to said cylinder to drive said piston, and a gauge and regulator to adjust said pressure.

8. A tester according to claim 7 in which springs are so disposed and arranged as adjustably to bias the brake pads against the blade, whereby to adjust said braking force.

9. A tester according to claim 7 in which a sensor is fixed to the base, so disposed and arranged as to signal the arrival of the holder at a desired limit.

10. A tester according to claim 7 in which a brake release is mounted to said base to release the brake pads from the blade to enable the target to be moved to a start position.

11. A tester according to claim 10 in which said blade includes an axial slot through which the brake release passes.

12. A tester according to claim 8 in which said brake pads are held in respective mounts one on each side of said blade, and in which a bolt passes through both of said mounts with a nut threaded to both ends and a spring between each nut and the respective mount, whereby when the nuts are tightened, the compressive force on the brake pads is adjustably increased.

* * * * *